United States Patent [19]

Hebky et al.

[11] 4,225,604

[45] Sep. 30, 1980

[54] 2-FORMYLQUINOXALINE-1,4-DIOXIDE CYANOACETYLHYDRAZONE AND METHODS FOR PREPARATION THEREOF

[75] Inventors: Jaromír Hebký; Vladimír Lupínek; Milan Sova, all of Prague; Bohumil Ševčík; Jiří Brož, both of Jílové u Prahy, all of Czechoslovakia

[73] Assignee: SPOFA, spojene podniky prop farmaceutickou vyrobu, Praha, Czechoslovakia

[21] Appl. No.: 930,067

[22] Filed: Aug. 2, 1978

[30] Foreign Application Priority Data

Aug. 2, 1977 [CS] Czechoslovakia ................... 5118/77

[51] Int. Cl.$^3$ ................. C07D 241/52; A67K 31/495
[52] U.S. Cl. ................................. 424/250; 544/353; 544/355; 426/532

[58] Field of Search .................. 544/353; 424/250

[56] References Cited

PUBLICATIONS

Benko et al., Chem. Abs. 85, 94406s (1976).
Gyar, Chem. Abs. 86, 72701c (1976).
Broz et al., J. Chem. Abs. 88, 151119p (1977).
Broz et al. II, Chem. Abs. 88, 188770 (1977).

*Primary Examiner*—Mark L. Berch

[57] ABSTRACT

2-Formylquinoxaline-1,4-dioxide cyanoacetylhydrazones evidence significant anticoccidial properties, enhance the feed conversion and stimulate the growth of farm animals. The described compositions are non-toxic and are suitable as veterinary medicaments and feed additives for such animals.

4 Claims, No Drawings

2-FORMYLQUINOXALINE-1,4-DIOXIDE CYANOACETYLHYDRAZONE AND METHODS FOR PREPARATION THEREOF

This invention relates to a method for the preparation of 2-formylquinoxaline-1,4-dioxide cyanoacetylhydrazones and to the resultant hydrazones.

Heretofore, it has been known that certain acylhydrazones in the 2-formylquinoxaline-1,4-dioxide family evidence antimicrobial action on grampositive and gramnegative microorganisms. In accordance with the present invention, it has been determined that cyanoacetylhydrazones in the 2-formyl-quinoxaline-1,4-dioxide family evidence similar antimicrobial characteristics to those of the parent compound and, additionally, evidence pronounced anticoccidial properties, promotory effects on the growth of farm animals and favorably influence the general health of such animals.

The cyanoacetylhydrazones of the invention are of the general formula

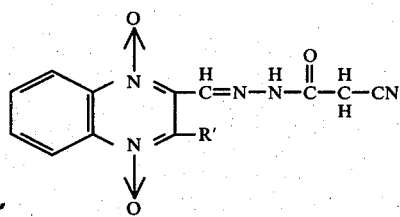
(1)

wherein R' is selected from the group consisting of hydrogen or an alkyl group of 1-4 carbon atoms. The described compounds may conveniently be prepared by any of the following preparative techniques:

(a) A 2-formylquinoxaline-1,4-dioxide of the general formula

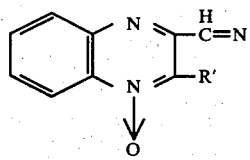
(2)

wherein R' is hydrogen or an alkyl group of 1-4 carbon atoms or an acetal-like functional derivative thereof may be reacted with cyanoacetylhydrazine of the formula $H_2N-NH-COOCH_2CN$. This reaction is conveniently effected in the presence of an inert organic or inorganic solvent or diluent. Materials found suitable for this purpose include aliphatic and aromatic hydrocarbons or halogenated derivatives thereof such as benzene, toluene, chlorobenzene, dichloromethane, chloroform, etc., carboxylic acids such as formic or acetic acid, aliphatic alcohols such as methanol, ethanol, etc., inorganic acids such as hydrochloric acid and mixtures thereof. This reaction may be conducted at temperatures ranging from 0° C. to the boiling point of the mixture over a time period ranging from several minutes to approximately 24 hours.

(b) A 2-formylquinoxaline 1,4-dioxide hydrazone of the general formula

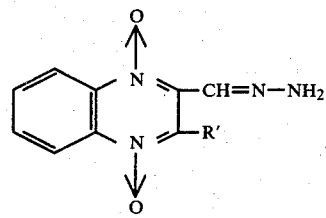
(3)

wherein R' is selected from among hydrogen and an alkyl group of 1-4 carbon atoms may be reacted with a reactive derivative of cyanoacetic acid, preferably cyanoacetyl chloride or a cyanoacetic acid ester such as a halogenated phenyl cyanoacetate. This reaction is effected in inert organic or inorganic solvent or diluent or mixtures thereof at temperatures ranging from −20° to +100° C.

The hydrazone employed in this reaction (3) may be obtained by reacting the parent 2-formylquinoxaline-1,4-dioxide with hydrazine. The reactive derivatives of cyanoacetic acid are well-known in the prior art and may be obtained by known methods.

(c) A 2-formylquinoxaline-1,4-dioxide of the general formula (2) set forth above may be reacted with chloroacetylhydrazine of the formula $H_2N-NH-COCH_2Cl$ (see J. S. Pizey et al, J. Sci. Agr. 10, 577, 1959) and, subsequently, reacted with an alkali metal cyanide in accordance with known techniques.

(d) A 2-formylquinoxaline-1,4-dioxide hydrazone of the general formula (3) set forth above may be reacted successively with chloroacetyl chloride in the presence of an organic or inorganic base, preferably a tertiary amine, in an inert organic or inorganic medium and, subsequently, with an alkali metal cyanide.

(e) A 2-formylquinoxaline-1,4-dioxide oxime of the general formula

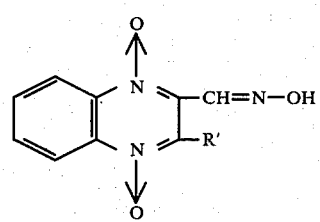

wherein R' is hydrogen or an alkyl group of 1-4 carbon atoms may be reacted with cyanoacetylhydrazine in an aqueous inorganic acid solution, preferably 30-98% sulfuric acid, at a temperature within the range of 20°-100° C.

In comparison with the known non-antibiotic animal growth promotants routinely employed by workers in the art, the compositions described herein evidence limited toxicity. Thus, a comparative study of the toxic properties of 2-formylquinoxaline-1,4-dioxide cyanoacetylhydrazone of the invention, identified as compound A, and the prior art 2-formylquinoxaline-1,4-dioxide methoxycarbonylhydrazone, identified as compound B, was made in a series of parallel experiments performed on male rats having body weights ranging from 190-240 grams and grouped in groups of 10 animals each. The compounds were administered orally in the form of a 2.5% suspension in an aqueous arabic gum solution. Single doses as high as 500 mg/kg (2 ml. of suspension) were given to the animals twice a day, at 9:00 a.m. and at 1:00 p.m. over a 5-day period. Thus, ten doses of compounds A and B were administered. Table I hereinbelow sets forth the mortality rate of individual animals upon administering the noted doses of each compound.

TABLE I

| | Mortality of Test Animals Following the Indicated Dosage | | |
|---|---|---|---|
| Control Group Rat No. | Compound B Overall Dose mg/kg | Test Group Rat No. | Compound A Overall Dose mg/kg |
| 1 | 2.5 | 1 | — |
| 2 | 1.5 | 2 | — |
| 3 | 2.0 | 3 | — |
| 4 | 5.0 | 4 | — |
| 5 | 2.0 | 5 | — |
| 6 | 2.0 | 6 | — |
| 7 | 3.0 | 7 | — |
| 8 | 3.0 | 8 | 4.5 |
| 9 | 4.0 | 9 | — |
| 10 | 3.0 | 10 | 5.0 |

As noted from Table I, compound A is markedly less toxic than compound B. All animals in the control group died whereas only 2 of the ten members treated with the compound of the invention perished. The animals were observed an additional 5 days following the administration of the last dose.

Using the standard testing technique, the $LD_{50}$ value of compound A on female Wister rats of body weights ranging from 140-160 grams was determined, the animals being divided into groups of ten. Compound A was administered orally, in a single dose, in the form of a 20% suspension in a Dorfman medium. Acute toxicity could not be determined by this technique since the maximum practical dosage of 5500 mg/kg was sublethal. Thus, the $LD_{50}$ of compound A is substantially higher than 5,500 mg/kg orally.

Further experimentation with the compounds of the invention upon administration to broiler chickens, piglets and hogs revealed that these compounds markedly stimulated their total performance by increasing liveweight gains, enhancing the use of feed mixtures, reducing the incidence of diarrhea in piglets, and improving their general health. These compounds may also be used alone or in combination with known veterinary medicaments for the prevention and treatment of salmonelloses and dysenterias in hogs and other farm animals.

Administration of the compounds described herein may be effected either in the pure state or in combination with common carriers, excipients and auxiliaries, in dispensing forms suitable for veterinary purposes and animal nutrition, preferably as concentrates and premixes suitable for the compounding of feed mixtures.

Several examples of the present invention are set forth below. It will be appreciated by those skilled in the art that these examples are solely for the purposes of exposition and are not to be construed as limiting.

The melting points set forth in such examples were determined on Kofler block and stand uncorrected.

EXAMPLE I

This example describes the preparation of 2-formylquinoxaline-1,4-dioxide cyanoacetylhydrazone by 2 methods.

Method A. A solution comprising 15.2 grams (0.08 mole) of 2-formylquinoxaline-1,4-dioxide in 150 ml. of ethanol was reacted with 7.9 grams (0.08 mole) of cyanoacetylhydrazine (m.p. 105°-107° C.), the mixture being stirred at room temperature for 4 hours. The precipitated crude product yield was 18.4 grams (85% of theoretical yield). Upon crystallization from dimethylformamide, yellow crystals melting at 250°-260° C. were obtained.

Method B. A mixture comprising 23.6 grams (0.1 mole) of 2-formylquinoxaline-1,4-dioxide dimethylacetal and 500 ml. of methanol was reacted with 200 ml. of concentrated hydrochloric acid. The mixture of reactants was agitated until complete dissolution was effected. Then, 10.5 grams (0.105 mole) of cyanoacetylhydrazine was added and the reaction mixture stirred for 3 hours at room temperature. The precipitated crude product was washed with methanol and dried, so yielding 24.4 grams (90% of theory) of a yellow substance melting at a temperature within the range of 255°-260° C.

EXAMPLE II

2-Formyl-3-methylquinoxaline-1,4-dioxide cyanoacetylhydrazone

A suspension comprising 20.4 grams (0.1 mole) of 2-formyl-3-methylquinoxaline-1,4-dioxide (m.p. of 180°-182° C.) and 9.9 grams (0.1 mole) of cyanoacetylhydrazine in 200 ml of ethanol was stirred for 4 hours at room temperature. The separated product was sucked off and washed with ethanol, so yielding 22.2 grams (78% of theoretical) of crude material. Upon crystallization from dimethylformamide, yellow crystals melting at a temperature within the range of 255°-260° C. were obtained.

EXAMPLE III

A commercially available feed mixture for feeding broiler chickens (identified as BR-1) was enriched by adding thereto 1%, by weight, of a feed supplement containing the following active ingredients:

| | | |
|---|---|---|
| 2-Formylquinoxaline-1,4-dioxide cyanoacetylhydrazone (Compound A) | mg. | 5,000 |
| Vitamin A | I.U. | 1,000,000 |
| Vitamin $D_3$ | I.U. | 100,000 |
| Vitamin $B_2$ | mg. | 313 |
| Vitamin $B_{12}$ | mg. | 2 |
| Vitamin $K_3$ | mg. | 200 |
| Niacin | mg. | 120 |
| Methionin | mg. | 100,000 |
| Amprol + ethopabate 25% premix | mg. | 50,000 |
| Ethoxyquine (antioxidant) | mg. | 12,500 |

The supplemented mixture was fed by standard feeding techniques to Tetra SL chickens. An increase in weight gain of 12.6% was observed. This compared favorably with a group of control chickens which were not fed the supplemented mixture and evidence 7% less weight gain.

The above-noted compound (hydrazone) was added to a BR-1 feed mixture in doses of 10, 20, 50 and 100 mg/kg of mixture and fed to Ross-1 broiler chickens. During the first 4 weeks of feeding the weight gains observed were 5.6%, 8.5%, 8.6%, and 5.6% greater than those in a control group. It was also noted that the feed converstion improved by a margin ranging from 0.9 to 5.3%.

EXAMPLE IV

A commercially available feed mixture, identified as COS-2 for feeding early-weaned piglets was enriched by admixing it with 1%, by weight, of the following feed supplement:

| Compound (A) | mg. | 5,000 |
|---|---|---|
| Vitamin A | I.U. | 800,000 |
| Vitamin D$_3$ | I.U. | 200,000 |
| Vitamin B$_2$ | mg. | 300 |
| Vitamin B$_6$ | mg. | 100 |
| Vitamin K$_3$ | mg. | 150 |
| Vitamin E | mg. | 3,000 |
| Vitamin C | mg. | 10,000 |
| Niacin | mg. | 1,000 |
| Calcium pantothenate | mg. | 500 |
| Lysine | mg. | 50,000 |
| Ethoxyquine | mg. | 12,500 |

Over a 28-day period, early weaned piglets were fed with the foregoing mixture. Weight gains evidenced by piglets so fed were 44.1% greater than the weight gains of piglets in a control group not fed the enriched feed. Additionally, the feed conversion rate improved by 20.9% over the control group. The procedure was repeated and weight gains were 39.9 and 33.7% greater than those of a control group. It was also noted that piglets fed the enriched feed did not evidence symptoms of diarrhea.

What is claimed is:

1. 2-Formylquinoxaline-1,4-dioxide cyanoacetylhydrazone of the formula

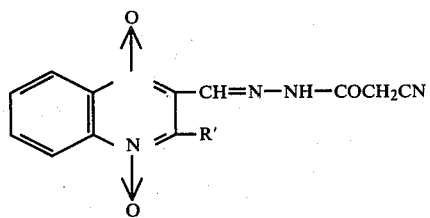

wherein R' is selected from the group consisting of hydrogen and an alkyl group of 1-4 carbon atoms.

2. 2-Formylquinoxaline-1,4-dioxide cyanoacetylhydrazone.

3. 2-Formyl-3-methyl-quinoxaline, 1,4-dioxide cyanoacetylhydrazone.

4. An anticoccidal and growth stimulating composition consisting essentially of an effective amount of a compound of the formula

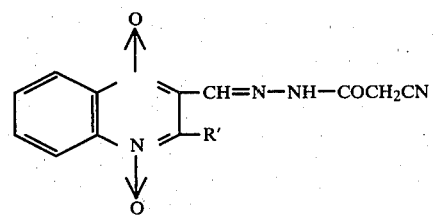

and a carrier suitable for veterinary purposes, $R^1$ being selected from the group consisting of hydrogen and an alkyl group of 1-4 carbon atoms.

* * * * *